(12) United States Patent
Wong

(10) Patent No.: US 12,303,191 B2
(45) Date of Patent: May 20, 2025

(54) SYSTEMS AND METHODS FOR POWERING AN ANTENNA

(71) Applicant: INTUITIVE SURGICAL OPERATIONS, INC., Sunnyvale, CA (US)

(72) Inventor: Serena H. Wong, Los Altos, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 1044 days.

(21) Appl. No.: 17/058,292

(22) PCT Filed: Jun. 11, 2019

(86) PCT No.: PCT/US2019/036541
§ 371 (c)(1),
(2) Date: Nov. 24, 2020

(87) PCT Pub. No.: WO2019/241242
PCT Pub. Date: Dec. 19, 2019

(65) Prior Publication Data
US 2021/0290303 A1  Sep. 23, 2021

Related U.S. Application Data

(60) Provisional application No. 62/684,597, filed on Jun. 13, 2018.

(51) Int. Cl.
*A61B 18/14* (2006.01)
*A61B 18/18* (2006.01)
(Continued)

(52) U.S. Cl.
CPC ........ *A61B 18/1815* (2013.01); *H01L 31/054* (2014.12); *A61B 2018/00023* (2013.01);
(Continued)

(58) Field of Classification Search
CPC ...... A61B 18/1815; A61B 2018/00791; A61B 2018/1861; A61B 2018/1823
See application file for complete search history.

(56) References Cited

U.S. PATENT DOCUMENTS 6,275,738 B1 * 8/2001 Kasevich ........... A61B 18/1815
607/101
6,380,732 B1   4/2002 Gilboa
(Continued)

FOREIGN PATENT DOCUMENTS

| EP | 2425871 A2 | 3/2012 |
| JP | H04196623 A | 7/1992 |
| WO | WO-2016191298 A1 | 12/2016 |

OTHER PUBLICATIONS

Beling A., et al., "High-power, High-linearity Photodiodes," Optica, Mar. 2016, vol. 3 (3), pp. 328-338.
(Continued)

*Primary Examiner* — Jaymi E Della
(74) *Attorney, Agent, or Firm* — Haynes & Boone, LLP.

(57) ABSTRACT

An antenna system comprises an elongate flexible member and an optical fiber extending within the elongate flexible member. The system also comprises an energy conversion device optically coupled to a distal end of the optical fiber. The energy conversion device is operable to convert an optical signal received from the optical fiber to an electrical signal. The system also includes an antenna body coupled to the energy conversion device and powered by the electrical signal from the energy conversion device.

19 Claims, 4 Drawing Sheets

(51) Int. Cl.
  *H01L 31/054* (2014.01)
  *A61B 18/00* (2006.01)
  *A61B 34/35* (2016.01)

(52) U.S. Cl.
  CPC .............. *A61B 2018/00577* (2013.01); *A61B 2018/00642* (2013.01); *A61B 2018/00791* (2013.01); *A61B 2018/1823* (2013.01); *A61B 2018/1861* (2013.01); *A61B 34/35* (2016.02)

(56) References Cited

U.S. PATENT DOCUMENTS

| | | | |
|---|---|---|---|
| 6,389,187 B1 | 5/2002 | Greenaway et al. | |
| 6,575,969 B1* | 6/2003 | Rittman, III | A61B 18/1482 606/41 |
| 7,316,681 B2 | 1/2008 | Madhani et al. | |
| 7,772,541 B2 | 8/2010 | Froggatt et al. | |
| 9,259,274 B2 | 2/2016 | Prisco | |
| 9,452,276 B2 | 9/2016 | Duindam et al. | |
| 2002/0116029 A1* | 8/2002 | Miller | A61N 1/056 607/9 |
| 2002/0116034 A1 | 8/2002 | Miller et al. | |
| 2003/0195500 A1* | 10/2003 | Moorman | A61B 18/1477 606/33 |
| 2003/0204207 A1* | 10/2003 | MacDonald | A61N 1/3752 607/9 |
| 2005/0245920 A1* | 11/2005 | Vitullo | A61B 18/18 607/156 |
| 2006/0013523 A1 | 1/2006 | Childers et al. | |
| 2008/0212082 A1* | 9/2008 | Froggatt | G02B 6/02042 356/73.1 |
| 2013/0204072 A1* | 8/2013 | Verard | A61B 6/032 600/7 |
| 2013/0267943 A1* | 10/2013 | Hancock | H05B 6/806 606/33 |
| 2014/0276200 A1* | 9/2014 | Brannan | A61B 18/1815 600/562 |
| 2016/0287885 A1 | 10/2016 | Saini | |
| 2017/0128119 A1* | 5/2017 | Lambert | A61B 5/1076 |
| 2021/0068897 A1 | 3/2021 | Wong | |
| 2021/0138195 A1 | 5/2021 | Blumenkranz | |

OTHER PUBLICATIONS

International Search Report and Written Opinion for Application No. PCT/US2019/036541, mailed on Sep. 6, 2019, 13 pages.

International Preliminary Report on Patentability for Application No. PCT/US2019/036541, mailed on Dec. 24, 2020, 8 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

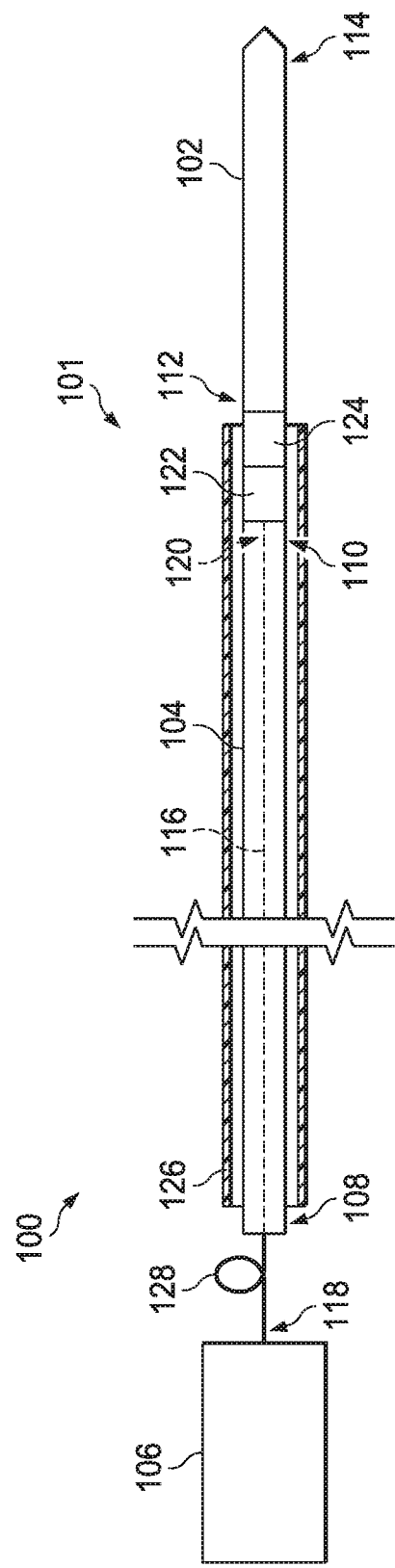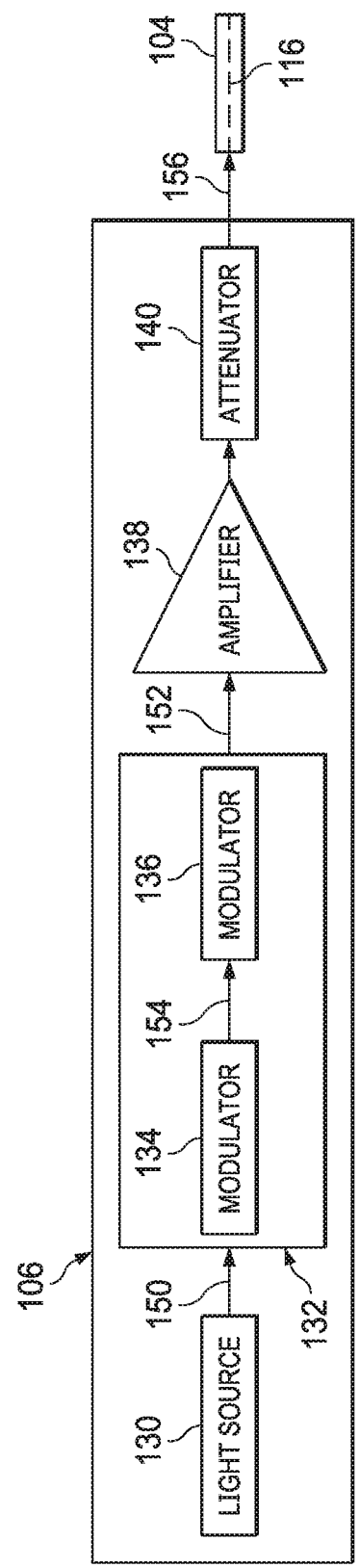

SYSTEMS AND METHODS FOR POWERING AN ANTENNA

CROSS-REFERENCE TO RELATED APPLICATIONS

This application is the U.S. national phase of International Application No. PCT/US2019/036541, filed Jun. 11, 2019, which designated the U.S. and claims priority to and the benefit of U.S. Provisional Application No. 62/684,597 filed Jun. 13, 2018, both of which are incorporated by reference herein in their entirety.

FIELD

The present disclosure is directed to systems and methods for powering a minimally invasive tissue ablation antenna with reduced thermal energy loss to the patient anatomy.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy.

Currently, flexible antennas that can be delivered to a target anatomy through an elongate minimally invasive device may have power limitations due to the thermal energy loss generated with conventional coaxial cable-based designs and the associated risk of burning the patient anatomy along the length of the coaxial cable. Systems and methods are needed that provide increased power to ablation antennas while reducing the thermal energy loss to the patient anatomy.

SUMMARY

The embodiments of the invention are best summarized by the claims that follow the description.

Consistent with some embodiments, an antenna system comprises an elongate flexible member and an optical fiber extending within the elongate flexible member. The system also comprises an energy conversion device optically coupled to a distal end of the optical fiber. The energy conversion device is operable to convert an optical signal received from the optical fiber to an electrical signal. The system also includes an antenna body coupled to the energy conversion device and powered by the electrical signal from the energy conversion device.

In another embodiment, a method comprises generating an optical signal and sending the optical signal along an optical fiber extending through an elongate flexible member. The method also comprises converting the optical signal to an electrical signal with an energy conversion device coupled to a distal end of the optical fiber and powering an antenna body coupled to the energy conversion device with the electrical signal.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 1 is a simplified diagram of an antenna system according to some embodiments.

FIG. 2 is a simplified diagram of a signal generation apparatus according to some embodiments.

Figure 3:
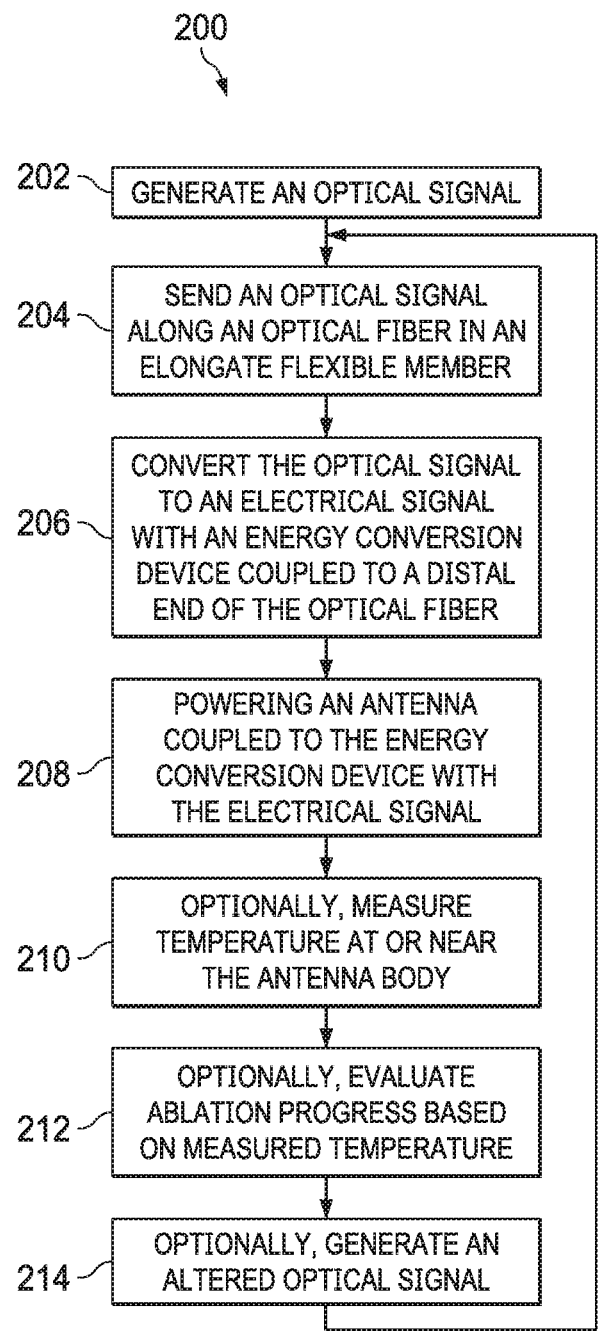
FIG. 3 is a flowchart illustrating a method for powering an antenna system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Minimally invasive medical procedures may include the use of tissue ablation devices. Tissue ablation may be accomplished by electrical energy from frequencies ranging from very low frequency up to microwave and higher. Antenna-based tissue ablation systems used for microwave ablation or other high-frequency ablation, may require the delivery of large amounts of power to the antenna. For example, in some embodiments, microwave ablation antennas may require power of approximately 30 Watts. In other embodiments, high-frequency ablation antennas may require power between approximately 10 Watts and 40 Watts. Traditional minimally invasive ablation antenna designs may use a coaxial cable to deliver power to the antenna. However, the high power requirements for high-frequency antennas combined with the small size needed for minimally invasive procedures may result in thermal energy loss along the coaxial cable that exceeds safety standards and results in burns to the patient anatomy. For example, non-target lung tissue may be harmed at a temperature of approximately 43° C. over time. Fluid circulation cooling systems may be used reduce the temperatures in coaxial cable-based antenna systems, but the conduits needed to circulate the cooling fluid may increase the diameter of the minimally invasive system and limit the system's access into small anatomic passageways. The systems and methods described herein may be used to power minimally-invasive, high-frequency antennas at safe temperatures.

FIG. 1 illustrates an antenna system 100 that may be suitable for use in, for example, surgical, diagnostic, therapeutic, or biopsy procedures. In some embodiments, however, the systems, instruments, and methods described herein may be used for animals, human cadavers, animal cadavers, portions of human or animal anatomy, non-surgical diagnosis, ex-vivo procedures, as well as for industrial systems and general robotic, teleoperational robotic, or manually operated systems.

As shown in FIG. 1, the antenna system 100 includes an antenna probe 101 and a signal generation apparatus 106. The antenna probe 101 can include an antenna body 102, an elongate flexible body 104. The elongate flexible body 104 has a proximal end 108 and a distal end 110. The antenna body 102 has a proximal end 112 and a distal end 114. An optical fiber 116 extends through the elongate flexible body 104 and is optically coupled at a proximal end 118 to the signal generation apparatus 106. A distal end of the optical fiber 116 may be optically coupled to an energy conversion device 122 that converts optical signals received from the optical fiber to electrical signals that may be used to power the antenna body 102. Optionally, a flexible conductive cable 124, such as a short length of coaxial cable, may be used to couple the energy conversion device 122 to the antenna body 102 and conduct the electrical signal from the energy conversion device 122 to the antenna assembly. The antenna probe 101 may be advanced and guided to a target location in a patient anatomy through a catheter assembly 126. The antenna probe 101 may be extendable distally beyond a distal end of the catheter assembly 126 to position the antenna body 102 near the target ablation site.

The antenna body 102 may be flexible to allow passage through the catheter assembly 126. For example, the antenna body 102 may be formed with one or more of a variety of generally cylindrical or tubular patterns including bar and ring patterns, cutout patterns, slotted patterns, and helical patterns. The antenna body could also consist of a number of wire/wires that may be formed from the coaxial cable that may be coupled to the energy conversion device. The antenna body 102 may be designed to bend through 10 to 15 mm bends and as low as 5 mm with the ability to recover for to a straightened configuration. In some embodiments, the antenna body 102 may be integrally formed with the cable 124. Various embodiments of a flexible antenna body are disclosed in U.S. Provisional Patent Application 62/649,974 (filed Mar. 29, 2018) (disclosing "Systems and Methods Related to Flexible Antennas"), which is incorporated by reference herein in its entirety.

The optional cable 124 may be a coaxial cable including an inner conductor surrounded by a dielectric insulator layer. An outer conductor may surround the dielectric insulator layer. A protective plastic jacket may surround the outer conductor.

The energy conversion device 122 may include one or more energy conversion units such as photodiodes that convert light into electrical current. A PIN diode may be an example of a suitable photodiode for receiving an optical signal from the optical fiber 116 and converting the optical signal to an electrical signal for powering the antenna 102. The electrical current from the photodiode may be delivered to the cable 124 or directly to the antenna 102 if a cable 124 is omitted. In various embodiments, the energy conversion device 122 may include a plurality of photodiodes. For example, the electrical output from an array of three or more photodiodes may be combined in parallel to power the antenna. The photodiodes may be relatively small with, for example, an active area of approximately 100 μm.

The optical fiber 116 may extend within a lumen of the elongate flexible body 104. A distal end 120 of the optical fiber 116 may be fixed to the energy conversion device 122. For example the distal end 120 may be directly coupled to one or more photodiodes. The proximal end 118 of the optical fiber 116 may include a service loop 128, providing float or play at the proximal end. Various embodiments disclosing the use of an optical fiber service loop are disclosed in U.S. Provisional Application 62/671,958 (filed May 15, 2018) (disclosing "Backend Mechanism of a Catheter Control System"), which is incorporated by reference herein in its entirety. The proximal end 118 is optically coupled to the signal generation apparatus 106 to receive generated light signals. Additionally, one or more wires may supply a biasing signal to the energy conversion device 122 to generate a bias voltage for operating the energy conversion device.

The optical fiber 116 may be a single core or a multi-core optical fiber. In various embodiments, in order to supply multiple optical signals to an array of photodiodes, multiple fibers or multiple cores in the same fiber can be used to transmit optical signals through the elongate flexible body 104. In some embodiments, using a multicore fiber may provide additional functionality to the device. Some of the cores may be used for measuring strain, or shape that provide additional information describing the elongated flexible device 104 including position, orientation, speed, velocity, pose, and/or shape of a distal end, distal section, and/or one or more sections of the ablation probe. In some embodiments, an optical fiber may be used to provide both shape sensing and to provide optical signals to the energy conversion device. Various example systems and methods for monitoring the shape of an optical fiber are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering.

In some embodiments, one or more of the cores may be used to measure temperature at or near the antenna body, which can be used to evaluate ablation (e.g. determine depth and extent of ablated tissue) providing for a closed loop control of the optical signals used to power the antenna body 102. In some embodiments, temperature measurements may be correlated with shape measurements to identify a temperature distribution along a length of the elongate flexible body which can be used to more accurately characterize ablation progress. In some embodiments, additional optical fibers may be integrated into the catheter body 126, elongate flexible body 104, and/or the antenna body 102 to measure strain, shape, force, and/or temperature along the length of the elongate body and/or antenna body. In some embodiments, one or more additional optical fibers may extend beyond a distal end of an optical fiber used to deliver an optical signal to an energy conversion device, extending along a length of an antenna body. For example, referring to FIG. 1, additional optical fibers may be integrated into a wall of elongate flexible body 104 and extend past distal end 110 along a length of antenna body 102. In alternative embodiments, one or more additional fibers used to measure strain, shape, force, and/or temperature, may be integrated within a wall of the catheter assembly 126.

FIG. 2 illustrates the signal generation apparatus 106 in greater detail, according to some embodiments. The signal generation apparatus may be located in a portion of the system 100 that resides outside of the patient anatomy while the elongate flexible body 104 and the antenna body 102 are inserted into the patient anatomy. The signal generation apparatus 106 may include a light source 130, such as a continuous wave light source. Light 150 generated by the light source 130 may be processed to create an optical signal. For example, the light 150 may be passed through a modulation system 132 to create a pulsed RF-modulated optical signal 152. The modulation system 132 may include a frequency modulator 134 that modulates the frequency of the light 150. In various embodiments, the frequency modulator 134 may generate a radio frequency (RF) modulated optical signal 154. The modulation system 132 may also include a pulse modulator 136 that modulates the optical signal 154 to generate a pulsed RF modulated optical signal 152. A pulsed signal 152 conveyed by the optical fiber 116 may aid in controlling the temperature of the photodiodes in the energy conversion device 122 and preventing overheating. The modulators 134, 136 may be, for example Mach-Zender modulators.

The modulated optical signal 152 may be further processed by other optical devices. For example, the optical signal 152 may be processed by an amplifier 138. For example, an erbium-doped fiber amplifier may amplify the signal 152. The optical signal may also be processed by an attenuator 140 to modify the power level of the signal. The optical signal 156 output from the signal generation apparatus 106 may be sent to the optical fiber 116. In various embodiments, some components of the signal generation apparatus 106 may be omitted or arranged in a different order.

FIG. 3 illustrates a method 200 for powering an antenna system according to some embodiments. The method 200 is illustrated in FIG. 3 as a set of operations or processes 202 through 208. Not all of the illustrated processes 202 through 208 may be performed in all embodiments of method 200. Additionally, one or more processes that are not expressly illustrated in FIG. 3 may be included before, after, in between, or as part of the processes 202 through 208. In some embodiments, one or more of the processes 202 through 208 may be implemented, at least in part, in the form of executable code stored on non-transitory, tangible, machine-readable media that when run by one or more processors (e.g., the processors of control system) may cause the one or more processors to perform one or more of the processes.

At process 202, an optical signal is generated by a signal generation apparatus such as signal generation apparatus 106. As an example, continuous wave light 150 may be generated by the light source 130. In one embodiment, the generated light may have a wavelength selected from a range between 650 and 3000 nm. In one embodiment, the generated light may have a wavelength of approximately 1550 nm. The light 150 may undergo frequency modulation at the modulator 134 to generate an RF modulated signal 154 and may be further processed by the pulse modulator 136 to generate a pulsed RF modulated optical signal 152. In various embodiments, the light may be modulated to a frequency between approximately 1-10 GHz. The light waveform may be pulsed to prevent overheating of the photodiodes in the energy conversion device. In various embodiments, a duty cycle of approximately 15% may be used to prevent overheating. The light signal may be further processed by, for example, additional modulators, filters, amplifiers, attenuators or other optical processing equipment to generate the output optical signal 156. In other examples, using other signal generation systems, the output optical signal may be modulated or continuous wave light adjusted to achieve an optical signal that may be converted by the energy conversion device into an electrical signal for powering the antenna.

At process 204, the output optical signal is sent to a flexible optical fiber extending through an elongate flexible member. For example, the output optical signal 156 may be sent to and transmitted along the fiber 116 extending through the elongate flexible member 104. Multiple output optical signals may be transmitted along a plurality of fibers extending through the elongate flexible or multiple output optical signals may be transmitted via a single fiber with multiple cores. In addition to the optical signal 156 that may be converted to power the antenna, other optical signals may be transmitted to bias the diodes of the energy conversion device. Other optical signals may also be transmitted and converted at the energy conversion device to power other electronic equipment at the distal end of the elongate flexible member.

At process 206, the optical signal is converted to an electrical signal by the energy conversion device coupled at the distal end of the optical fiber. For example, pulsed RF optical signal 156 may be converted by an array of PIN photodiodes in the energy conversion device 122 into a microwave electrical signal. While the pulsed optical signal may help prevent the temperature of the photodiodes from rising to a level that damages the photodiodes or causes injury to the patient, the energy conversion device may be further cooled using a circulating gas or fluid cooling system.

At a process 208, the electrical energy from the energy conversion device is used to power the antenna to provide ablation treatment to the patient. For example, the microwave electrical signal from the energy conversion device 122 may be used to power the microwave antenna 102. In various embodiments, power of approximately 10-35 Watts may be generated by the energy conversion device to power the microwave antenna. Optionally, the microwave electrical signal may be transmitted via a coaxial cable 124 portion of an antenna assembly that couples the energy conversion device 122 to the antenna body 102. Optionally, the coaxial cable may be cooled using a circulating fluid cooling system.

At an optional process 210, temperature may be measured at or near the antenna body. For example, one or more of the cores of the optical fiber 116 may be used to measure the temperature of tissue proximate the antenna body or another optical fiber may be embedded in the wall of the elongate flexible body and used to measure temperature. At an optional process 212, ablation progress may be evaluated (e.g. determine depth of ablation and/or extent of ablated tissue) based on the measured temperature. In some embodiments, temperature measurements may be correlated with shape measurements to identify a temperature distribution along a length of the elongate flexible body which can be used to more accurately characterize ablation progress. Temperature and/or shape may be measured using separate cores of optical fiber 116 or each may be measured by an additional or a plurality of optical fibers embedded within the wall of the elongate flexible body. Because the temperature and shape measurements are either made within the same fiber or within fibers that are embedded in the same flexible body, the relative positions measurement cores/fibers are known, so the temperature measurements may be correlated to the shape measurements.

At an optional process 214, an altered optical signal may be generated to adjust for a desired ablation. For example, the altered optical signal may be generated to increase or decrease ablation power and/or ablation duration. After the optional processes 210-214, the method may return to process 204.

Figure 4:
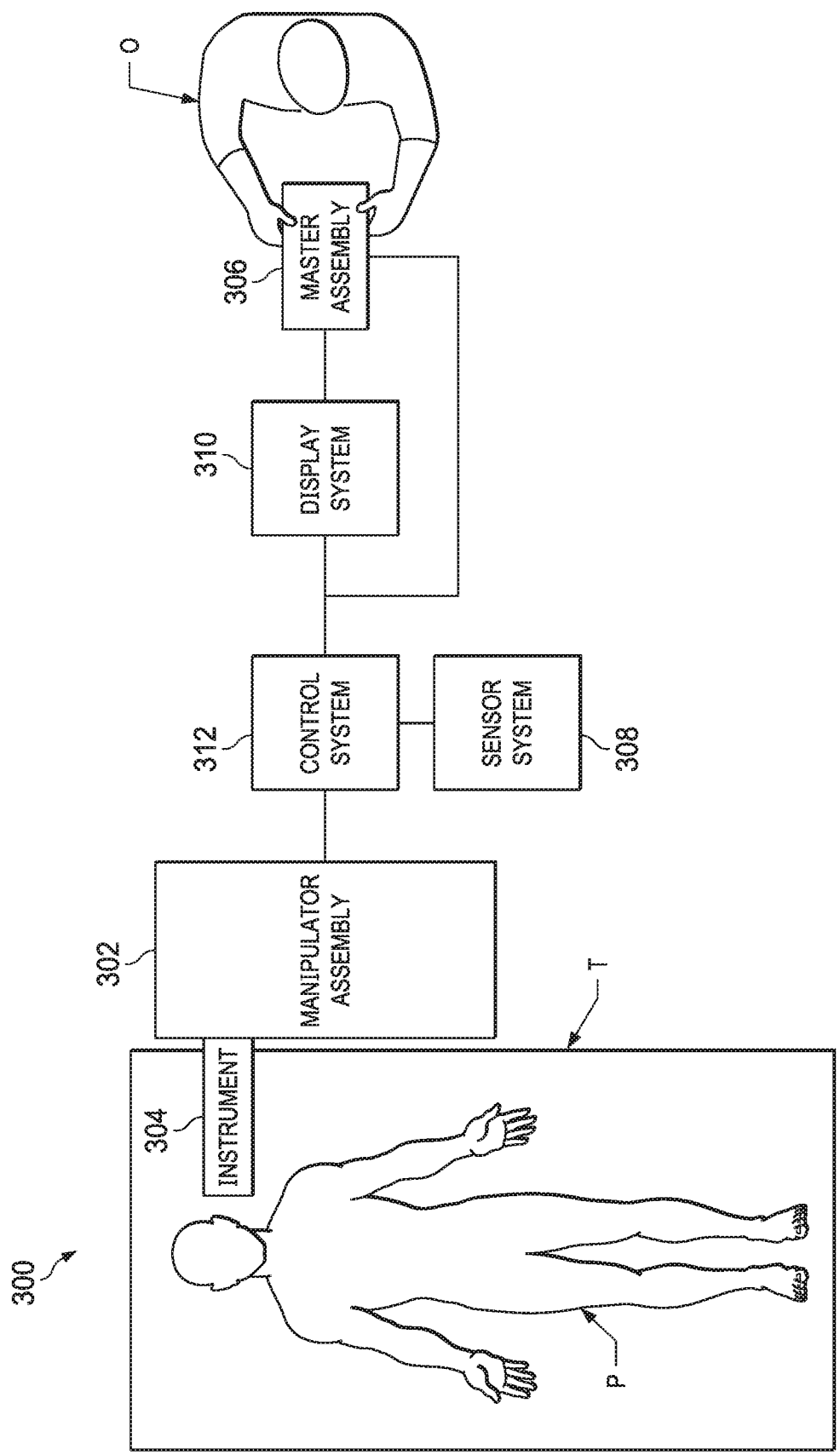
FIG. 4 is a simplified diagram of a teleoperated medical system according to some embodiments.

In some embodiments, the antenna system 100 may be used with a teleoperated medical system. For example, the catheter 126 or the elongated flexible body 104 may be remotely steerable and/or may be teleoperatively advanced into the patient anatomy. Further the signal generation apparatus may be controlled and monitored by a control system of a teleoperated medical system. FIG. 4 is a simplified diagram of a robotic and/or teleoperated medical system 300 according to some embodiments. In some embodiments, medical system 300 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 4, medical system 300 generally includes a manipulator assembly 302 for operating a medical instrument 304 (e.g. catheter 126, ablation probe 101, etc.) in performing various procedures on a patient P. Medical instrument 304 may extend into an internal surgical site within the body of patient P via an opening in the body of patient P. The manipulator assembly 302 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 302 is mounted to or near an operating table T. A master assembly 306 allows an operator O (e.g., a surgeon, a clinician, or a physician as illustrated in FIG. 4) to view the interventional site and to control manipulator assembly 302.

Master assembly 306 may be located at an operator console and generally includes one or more control devices for controlling manipulator assembly 302 which supports medical instrument 304. The control devices may include any number of a variety of input devices, such as joysticks, trackballs, data gloves, trigger-guns, hand-operated controllers, voice recognition devices, body motion or presence sensors, and/or the like.

Medical system 300 also includes a display system 310 for displaying an image or representation of the surgical site and medical instrument 304. Display system 310 and master assembly 306 may be oriented so operator O can control medical instrument 304 and master assembly 306 with the perception of telepresence. Display system 310 may also display an image of the surgical site and medical instruments captured by a visualization system which may include an image capture assembly that records a concurrent or real-time images of a surgical site and provides the image to the operator O through one or more displays of display system 310. The concurrent image may be, for example, a two or three dimensional image captured by an endoscope positioned within the surgical site. The visualization system may be implemented as hardware, firmware, software or a combination thereof which interact with or are otherwise executed by one or more computer processors, which may include the processors of a control system 312.

In some examples, display system 310 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity-based information) images and/or as images from anatomic models created from the pre-operative or intra-operative image data sets.

Medical system 300 may also include control system 312. Control system 312 includes at least one memory and at least one computer processor (not shown) for effecting control between medical instrument 304, master assembly 306, sensor system 308, and display system 310. Control system 312 also includes programmed instructions (e.g., a non-transitory machine-readable medium storing the instructions) to implement some or all of the methods described in accordance with aspects disclosed herein, including instructions for providing information to display system 310. While control system 312 is shown as a single block in the simplified schematic of FIG. 1, the system may include two or more data processing circuits with one portion of the processing optionally being performed on or adjacent to manipulator assembly 302, another portion of the processing being performed at master assembly 306, and/or the like. The processors of control system 312 may execute instructions comprising instruction corresponding to processes disclosed herein and described in more detail below. In some embodiments, control system 312 may receive force and/or torque feedback from medical instrument 304. Responsive to the feedback, control system 312 may transmit signals to master assembly 306. In some examples, control system 312 may transmit signals instructing one or more actuators of manipulator assembly 302 to move medical instrument 304.

Figure 5A:
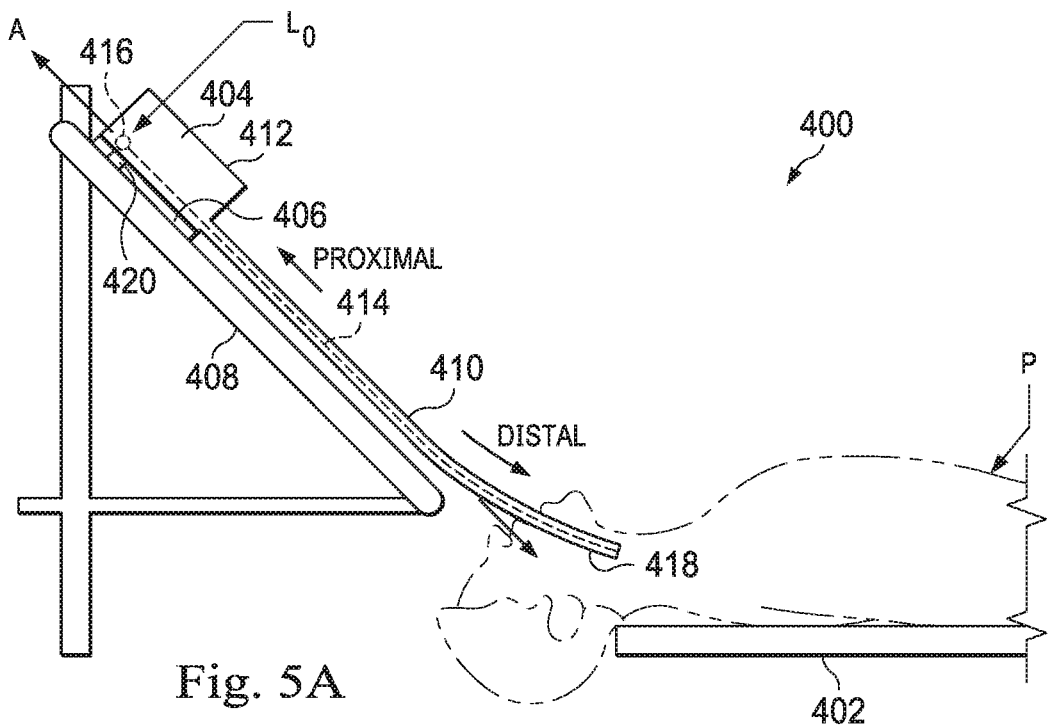
FIGS. 5A and 5B are simplified diagrams of side views of a patient coordinate space including a medical instrument mounted on an insertion assembly according to some embodiments.
Figure 5B:
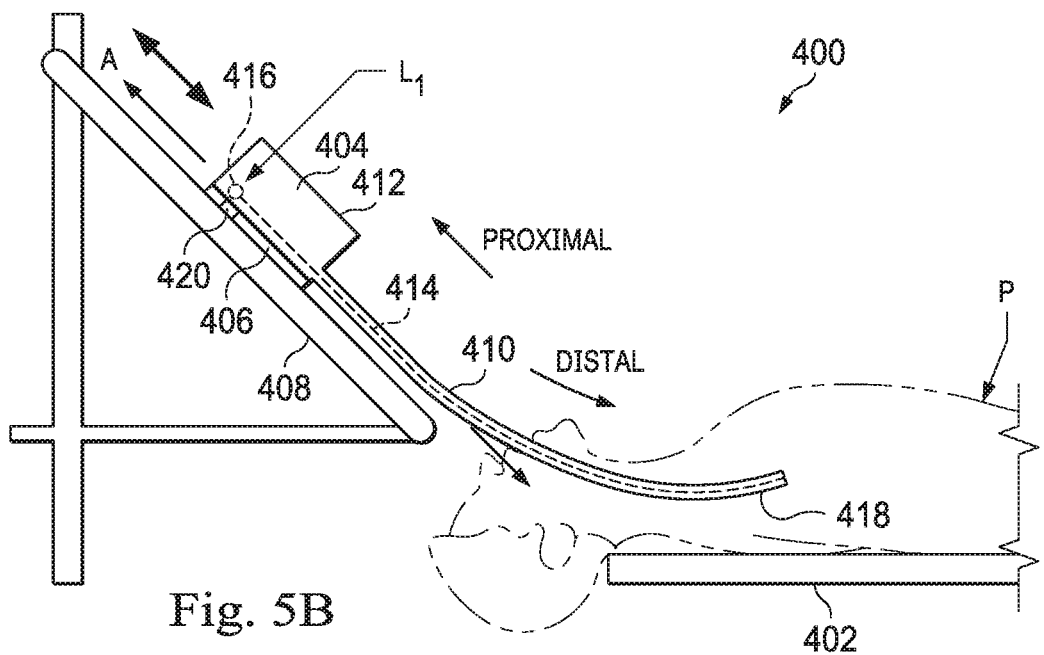

FIGS. 5A and 5B are simplified diagrams of side views of a patient coordinate space including a medical instrument mounted on an insertion assembly according to some embodiments. As shown in FIGS. 5A and 5B, a surgical environment 400 including a patient P is positioned on the table T of FIG. 1. Within surgical environment 400, a medical instrument 404 is used to perform a medical procedure which may include, for example, surgery, biopsy, ablation, illumination, irrigation, suction, or a system registration procedure. The medical instrument 404 includes a flexible elongate device 410 (e.g., a catheter) coupled to an instrument body 412.

FIG. 5A shows instrument body 412 and instrument carriage 406 in a retracted position along insertion stage 408. In this retracted position, the proximal point 416 is at a position $L_0$ on axis A. In FIG. 5B, instrument body 412 and instrument carriage 406 have advanced along the linear track of insertion stage 408 and distal end 418 of elongate device 410 has advanced into patient P. In this advanced position, the proximal point 416 is at a position $L_1$ on the axis A. In some examples, encoder and/or other position data from one or more actuators controlling movement of instrument carriage 406 along insertion stage 408 and/or one or more position sensors associated with instrument carriage 406 and/or insertion stage 408 is used to determine the position $L_x$ of proximal point 416 relative to position $L_0$. A sensor device 420, which may be a component of the sensor system 308, may provide information about the position of instrument body 412 as it moves on insertion stage 408 along insertion axis A. Sensor device 420 may include resolvers, encoders, potentiometers, and/or other sensors that determine the rotation and/or orientation of the actuators controlling the motion of instrument carriage 406 and consequently the motion of instrument body 412. In some embodiments, insertion stage 408 is linear. In some embodiments, insertion stage 408 may be curved or have a combination of curved and linear sections. In some examples, position $L_x$ may further be used as an indicator of the distance or insertion depth to which distal end 418 of elongate device 410 is inserted into the passageways of the anatomy of patient P.

In some examples, elongate device 410 may also include one or more sensors (e.g., components of the sensor system 308). In some embodiments, an optical fiber shape sensor 414 is fixed at a proximal point 416 on instrument body 412. In some examples, elongate device may be ablation probe xx, and optical fiber shape sensor 414 may be optical fiber 116. Optical fiber 414/116 may be used for both shape sensing and for providing optical signals to energy conversion device 122. In some embodiments, proximal point 416 of optical fiber shape sensor 414 may be movable along with instrument body 412 but the location of proximal point 416 may be known (e.g., via a tracking sensor or other tracking device). Shape sensor 414 may be aligned with flexible elongate device 410 (e.g., provided within an interior channel (not shown) or mounted externally) and measures a shape from proximal point 416 to another point such as distal end 418 of elongate device 410, thus determining the shape of flexible elongate device 410. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In various embodiments, a series of position sensors may be positioned along the elongate device 410 and then used for shape sensing. In some embodiments, position sensors may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

Elongate device 410 may also house cables, linkages, or other steering controls (not shown) that extend between instrument body 412 and distal end 418 to controllably bend distal end 418. In some examples, at least four cables are used to provide independent "up-down" steering to control a pitch of distal end 418 and "left-right" steering to control a yaw of distal end 418. Steerable elongate devices are described in detail in U.S. patent application Ser. No. 13/274,208 (filed Oct. 14, 2011) (disclosing "Catheter with Removable Vision Probe"), which is incorporated by reference herein in its entirety. The instrument body 412 may include drive inputs that removably couple to and receive power from drive elements, such as actuators, of the teleoperational assembly.

Instrument body 412 may be coupled to instrument carriage 406. Instrument carriage 406 is mounted to an insertion stage 408 fixed within surgical environment 400. Alternatively, insertion stage 408 may be movable but have a known location (e.g., via a tracking sensor or other tracking device) within surgical environment 400. Instrument carriage 406 may be a component of a manipulator assembly (e.g., manipulator assembly 302) that couples to medical instrument 404 to control insertion motion (i.e., motion along the A axis) and, optionally, motion of a distal end 418 of an elongate device 410 in multiple directions including yaw, pitch, and roll. Instrument carriage 406 or insertion stage 408 may include actuators, such as servomotors, (not shown) that control motion of instrument carriage 406 along insertion stage 408.

The medical instrument 404 may be, for example, the instrument 304, which may include flexible elongate device 410 coupled to instrument body 412. Instrument body 412 may be coupled to instrument carriage 406 providing for advancement of medical instrument 404 along axis A. In one example, elongate device 410 may be catheter assembly 126 and may include one or more channels (not shown) sized and shaped to receive a medical tool (not shown) and the medical tool may be, for example, components of the antenna system 100 (e.g. antenna probe xx). Elongate device 410 and instrument body 412 may include drive systems to move or bend the distal end of elongate device 410 in multiple degrees of freedom. In another example, elongate device 410 may be ablation probe xx which may be actuated by drive systems to move or bend the distal end of ablation probe xx in multiple degrees of freedom and insert along Axis A using instrument carriage 406.

Referring back to FIG. 4, control system 312 may optionally include a virtual visualization system to provide navigation assistance, for example by providing a navigational path, to operator O when controlling medical instrument 304 during an image-guided medical procedure. Virtual navigation using the virtual visualization system may be based upon reference to an acquired preoperative or intraoperative dataset of anatomic passageways. Software, which may be used in combination with operator inputs, is used to convert the recorded images into segmented two dimensional or three-dimensional composite representation of a partial or an entire anatomic organ or anatomic region. An image data set is associated with the composite representation. An anatomical target area may be identified for treatment (e.g. ablation) and displayed on the composite representations of patient anatomy and a path to the anatomical target area may be planned.

The virtual visualization system obtains sensor data from sensor system 308 (e.g. fiber optic shape sensors, EM sensors, resolvers, encoders, potentiometers as previously described) that is used to compute an approximate location of medical instrument 304 with respect to the anatomy of patient P. The system may implement the sensor system 308 to register and display the medical instrument together with the preoperatively or intraoperatively recorded surgical images. For example, PCT Publication WO 2016/191298 (published Dec. 1, 2016) (disclosing "Systems and Methods of Registration for Image Guided Surgery"), which is incorporated by reference herein in its entirety, discloses such one system. Various systems for using fiber optic sensors to register and display a surgical instrument with surgical images are provided in PCT Publication WO 2016/191298 (published Dec. 1, 2016) (disclosing "Systems and Methods of Registration for Image Guided Surgery"), which is incorporated by reference herein in its entirety. Then, in some embodiments, often for purposes of image-guided medical procedures, display system 310 may display a virtual navigational image in which the actual location of medical instrument 304 is registered (i.e., dynamically referenced) with the preoperative or concurrent images/model. This may be done to present the operator O with a virtual image of the internal surgical site from a viewpoint of medical instrument 304.

In some embodiments, an optical fiber of the sensor system 308 (or another optical fiber in the medical instrument 304 may be used to measure temperature near an anatomical target ablation site. The ablation of the target tissue may be assessed using the temperature measurement. Information representing the assessment (e.g., an area of the ablation, a depth of ablation, a shape of an ablation zone, a sufficiency of ablation) may then be displayed with or on the anatomic model. For example, a composite representation of the anatomic model may be overlaid with a graphical indication of the region of ablation. Because the same fiber sensor or medical instrument (which is registered to the anatomic model) is used for both localization and temperature measurement, the location of the temperature measurement relative to the model is known. The ablation probe may then be repositioned in real time using the composite representation and the real-time known position of the ablation probe if the ablation is insufficient in size, shape, or amount, and energy can be re-delivered to perform an additional ablation. In some embodiments, the system controller may additionally use the assessment of ablation to alter ablation power and/or ablation duration to achieve a desired ablation of the target tissue. In some embodiments, an indicator or instructions may be provided or displayed with or overlaid on the composite representation of the anatomic model, to help guide a user in re-positioning of the ablation probe. The re-positioning of the probe may be manually performed by a user, may be performed by a tele-operated robotic surgical system controlled by the user, or may be automatically performed by a robotic surgical system. The indicator or instructions may be provided as visual graphics, visual instructions, audible instructions or alerts, and/or as haptic feedback (e.g. haptic vibration of inputs or audible louder/more frequent beeps as an ablation probe is positioned closer to a new target location).

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An antenna system comprising:
   a signal generator apparatus comprising a frequency modulator and a pulse modulator, the signal generator apparatus configured to generate a pulsed radiofrequency (RF) modulated optical signal by modulating light; and
   an antenna probe, comprising:
      an elongate flexible member;
      an optical fiber extending within the elongate flexible member and coupled at its proximal end to the signal generator apparatus;
      an energy conversion device optically coupled to a distal end of the optical fiber, the energy conversion device operable to convert the pulsed RF modulated optical signal received from the signal generator apparatus via the optical fiber to an electrical signal; and
      an antenna body coupled to the energy conversion device and configured to be powered by the electrical signal from the energy conversion device.

2. The antenna system of claim 1 wherein the electrical signal is a microwave electrical signal.

3. The antenna system of claim 1 wherein the energy conversion device includes at least one photodiode.

4. The antenna system of claim 3 wherein the at least one photodiode has an active area of approximately 100 µm.

5. The antenna system of claim 1, wherein the energy conversion device is configured to generate the electrical signal having approximately 30 W of power.

6. The antenna system of claim 1 wherein the optical fiber is configured to provide a shape measurement.

7. The antenna system of claim 1, wherein the optical fiber is configured to provide a temperature measurement.

8. The antenna system of claim 1, further comprising a coaxial cable extending between the energy conversion device and the antenna body, the coaxial cable configured to transfer the electrical signal from the energy conversion device to the antenna body.

9. A method comprising:
   generating, by a frequency modulator and a pulse modulator of a signal generator apparatus, a pulsed RF modulated optical signal by modulating light;
   sending the pulsed RF modulated optical signal along an optical fiber extending through an elongate flexible member and coupled at its proximal end to a signal generator apparatus;
   converting, by an energy conversion device coupled to a distal end of the optical fiber, the pulsed RF modulated optical signal received from the signal generator apparatus via the optical fiber to an electrical signal; and
   powering an antenna body coupled to the energy conversion device with the electrical signal.

10. The method of claim 4, further comprising applying a bias voltage to bias the energy conversion device, wherein a biasing signal is supplied along the optical fiber to generate the bias voltage.

11. The method of claim 9, wherein generating the pulsed RF modulated optical signal includes modulating the light to form an RF modulated optical signal and modulating the RF modulated optical signal to form the pulsed RF modulated optical signal.

12. The method of claim 9, further comprising:
   obtaining a temperature measurement for an area proximate the elongate flexible member.

13. The method of claim 12, further comprising:
   performing an evaluation based on the temperature measurement; and
   generating an altered pulsed RF modulated optical signal based on the evaluation.

14. The method of claim 12, further comprising:
   identifying a target location in an anatomic model based on the temperature measurement.

15. The method of claim 12, further comprising:
   receiving an anatomic model;
   obtaining shape data from the optical fiber;
   performing a registration between the anatomic model and the elongate flexible member based on the shape data;
   receiving a location for an anatomical treatment target area within the anatomical model; and
   displaying at least a portion of the anatomical model with a graphical representation of the anatomical treatment target area.

16. The method of claim 15 wherein powering the antenna body ablates the anatomical treatment target area.

17. The method of claim 16, further comprising:
   evaluating the ablation of the anatomical treatment target area based on the temperature measurement.

18. The method of claim 17, further comprising:
   updating the graphical representation based on the evaluation; and
   displaying the updated graphical representation.

19. The method of claim 9, wherein powering the antenna body coupled to the energy conversion device with the electrical signal comprises transferring the electrical signal from the energy conversion device to the antenna body via a coaxial cable extending between the energy conversion device and the antenna body.

* * * * *